US006350717B1

United States Patent
Frenzel et al.

(10) Patent No.: US 6,350,717 B1
(45) Date of Patent: Feb. 26, 2002

(54) CATALYST AND PROCESS FOR THE SELECTIVE HYDROGENATION OF UNSATURATED COMPOUNDS IN HYDROCARBON STREAMS

(75) Inventors: Andrea Frenzel, Limburgerhof; Cristina Freire Erdbrügger, Freinsheim; Ekkehard Schwab, Neustadt; Michael Hesse, Worms; Gerd Linden, Heidelberg; Herbert Wanjek, Maxdorf; Hans-Martin Allmann, Neunkirchen, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/385,458

(22) Filed: Aug. 30, 1999

(30) Foreign Application Priority Data

Sep. 4, 1998 (DE) .......................................... 198 40 373

(51) Int. Cl.⁷ .......................... B01J 23/58; B01J 23/40; B01J 23/72; B01J 23/56; B01J 23/44
(52) U.S. Cl. ...................... 502/330; 502/327; 502/331; 502/332; 502/333; 502/334; 502/335; 502/337; 502/339; 502/344; 502/345; 502/346; 502/347; 502/348
(58) Field of Search ............................... 502/327, 331, 502/332, 333, 334, 335, 337, 339, 344, 345, 346, 347, 348

(56) References Cited

U.S. PATENT DOCUMENTS

| | | | | |
|---|---|---|---|---|
| 3,821,323 A | | 6/1974 | Schulze et al. ............. 260/677 |
| 3,898,183 A | * | 8/1975 | Sugier et al. ................ 252/462 |
| 4,134,860 A | * | 1/1979 | Hindin et al. ........... 252/466 PT |
| 4,171,287 A | * | 10/1979 | Keith .......................... 252/462 |
| 4,407,733 A | * | 10/1983 | Birkenstock et al. ....... 502/174 |
| 4,409,410 A | | 10/1983 | Cosyns et al. .............. 585/259 |
| 4,490,481 A | | 12/1984 | Boitiaux et al. ............. 502/330 |
| 4,492,770 A | * | 1/1985 | Blanchard et al. .......... 502/304 |
| 4,517,395 A | | 5/1985 | Obenaus et al. ............. 585/259 |
| 4,533,779 A | | 8/1985 | Boitiaux et al. ............. 585/259 |
| 5,258,349 A | * | 11/1993 | Dalla Bett et al. .......... 502/330 |
| 5,356,851 A | | 10/1994 | Sarrazin et al. ............. 502/185 |
| 5,364,998 A | | 11/1994 | Sarrazin et al. ............. 585/259 |
| 5,648,576 A | | 7/1997 | Than et al. .................. 585/260 |
| 5,889,187 A | | 3/1999 | Than et al. .................. 585/260 |
| 5,948,377 A | * | 9/1999 | Sung ........................ 423/213.5 |
| 5,955,397 A | | 9/1999 | Didillon et al. ............. 502/339 |
| 6,074,973 A | * | 6/2000 | Lampert et al. ............... 502/60 |

FOREIGN PATENT DOCUMENTS

| | | |
|---|---|---|
| EP | 064301 | 11/1982 |
| EP | 087980 | 9/1983 |
| EP | 722776 | 7/1996 |
| EP | 738540 | 10/1996 |
| EP | 780155 | 6/1997 |
| EP | 992284 | 4/2000 |
| JP | 89/110594 | 4/1989 |

OTHER PUBLICATIONS

Allman et al., *DGMK–Conf.*, 11/11–12/93, pp. 1–30.
Derrien, *Cat. Hydrogen.*, vol. 27, pp. 613–666, 1986.
Boitiaux et al., *Hydrogenation*, Mar. 1985, 51–59.
Boitiaux et al., *DGMK–Conf.*, 11/11–12/93, pp. 49–57.

* cited by examiner

*Primary Examiner*—Steven P. Griffin
*Assistant Examiner*—Cam N. Nguyen
(74) *Attorney, Agent, or Firm*—Keil & Weinkauf

(57) ABSTRACT

A catalyst comprising at least one metal of the 10th group of the Periodic Table of the Elements and at least one metal of the 11th group of the Periodic Table of the Elements on an aluminum oxide support, wherein the metal or metals of the 10th group is or are essentially concentrated in an outer layer close to the surface of the catalyst particle, the metal or metals of the 11th group is or are distributed essentially uniformly over the volume of the catalyst particle and the weight ratio of the metal or metals of the 11th group to the metal or metals of the 10th group is not more than 1.95.

6 Claims, No Drawings

CATALYST AND PROCESS FOR THE SELECTIVE HYDROGENATION OF UNSATURATED COMPOUNDS IN HYDROCARBON STREAMS

FIELD OF THE INVENTION

The present invention relates to catalysts comprising noble metals on an aluminum oxide support and a process for the selective hydrogenation of unsaturated compounds in hydrocarbon streams using these catalysts. In particular, the present invention relates to catalysts comprising noble metals on an aluminum oxide support and a process for the selective hydrogenation of alkynes and/or alkadienes in C2 or C3 hydrocarbon streams in which they are present.

In refineries and petrochemical plants, large quantities of hydrocarbon streams are produced, stored and processed. Unsaturated compounds are frequently present in these hydrocarbon streams and their presence is known to lead to problems, particularly in processing and/or storage, or they are not the desired product and are therefore undesirable components of the respective hydrocarbon streams. General overviews of such problems in steam crackers and customary solutions have been given, for example, by H.-M. Allmann, Ch. Herion and P. Polanek in their paper "Selective Hydrogenations and Purifications in the Steamcracker Downstream Treatment" at the DGMK conference "Selective Hydrogenation and Dehydrogenation" on Nov. 11 and 12, 1993, in Kassel, Germany, the manuscript of which has also appeared in Conference Report 9305 of the DGMK Deutsche Wissenschaftliche Gesellschaft für Erdöl, Erdgas und Kohle e. V., Hamburg, pp. 1–30 (ISSN 0938-068X, ISBN 3-928164-61-9), and M. L. Derrien in: L. Cerveny (Editor), Stud. Surf. Sci. Catal., Volume 27, pp. 613–666, Elsevier, Amsterdam 1986.

In C2 streams from steam crackers, the secondary component acetylene is usually undesirable, and in C3 streams the secondary components propyne and allene are usually undesirable.

Analogous problems occur in the case of hydrocarbon streams which come from an FCC cracker or a reformer instead of a steam cracker. A general overview of such problems has been given, for example, by J. P. Boitiaux, C. J. Cameron, J. Cosyns, F. Eschard and P. Sarrazin in their paper "Selective Hydrogenation Catalysts and Processes: Bench to Industrial Scale" at the DGMK conference "Selective Hydrogenation and Dehydrogenation" on November 11 and 12, 1993 in Kassel, Germany, the manuscript of which has also appeared in Conference Report 9305 of the DGMK Deutsche Wissenschaftliche Gesellschaft für Erdöl, Erdgas and Kohle e. V., Hamburg, pp. 49–57 (ISSN 0938-068x, ISBN 3-928164-61-9).

In general, therefore, unsaturated compounds having triple bonds (alkynes, especially acetylene and propyne, the latter also known as "methylacetylene") usually have to be removed from C2 and C3 hydrocarbon streams and/or, in the case of C3 streams, unsaturated compounds having more than one double bond (alkadienes, especially propadiene, also known as "allene") have to be removed, in order to obtain the desired products such as ethylene and/or propylene in the quality required.

The removal of undesired unsaturated compounds from hydrocarbon streams in which they are present is frequently carried out by selective hydrogenation of some or all of the undesired unsaturated compounds in the hydrocarbon stream in question, preferably by selective hydrogenation to form more saturated compounds which do not cause problems and particularly preferably to form the components of the hydrocarbon stream which represent the desired products. For example, acetylene is hydrogenated to ethylene in C2 streams and propyne and propadiene are hydrogenated to propylene in C3 streams.

Such compounds typically need to be removed completely or at least to residual contents of a few ppm by weight. The ("over") hydrogenation to form compounds which are more saturated than the desired product and/or the parallel hydrogenation of a desired product containing one or more multiple bonds to give the corresponding more highly or completely saturated compound should, however, be avoided if possible because of the loss of valuable product associated therewith. The selectivity of the hydrogenation of the undesired unsaturated compounds therefore has to be as high as possible. In addition, a sufficiently high activity of the catalyst and a long operating life are generally desired. At the same time, the catalyst should not promote any other undesirable secondary reactions. Use is customarily made of supported noble metal catalysts in which noble metal is deposited on a catalyst support. Palladium is frequently used as noble metal and the support is generally a porous inorganic oxide, for example silica, aluminosilicate, titanium dioxide, zirconium dioxide zinc aluminate, zinc titanate, spinels and/or mixtures of such supports, but aluminum oxide or silicon dioxide are usually used. In addition, promoters or other additives may also be present. Processes for the selective hydrogenation of unsaturated compounds in hydrocarbon streams in which they are present are known both as a liquid-phase hydrogenation or mixed gas/liquid-phase hydrogenation, in the downflow or upflow mode, and as a pure gas-phase hydrogenation. Various process engineering measures for improving the selectivity have been disclosed for these processes.

DESCRIPTION OF THE PRIOR ART

For example, EP-A 87 980 teaches such a process in a fixed-bed reactor in which the hydrogen for hydrogenation is fed in at least two points along the reactor, thereby achieving a higher selectivity. EP-A 81 041 teaches that the addition of carbon monoxide reduces the hydrogenation and isomerization activity of the palladium used as catalyst metal and thus increases the selectivity. JP-A 01-110 594 teaches the addition of further electron donor compounds, either in the form of a dopant in the catalyst, for example alkali metals, or in the form of an addition to the reaction mixture, for instance of alcohols, ethers or nitrogen-containing compounds.

The use of promoters or dopants in addition to the actual hydrogenation-active catalyst metal is also known.

Thus, J. P. Boitiaux, J. Cosyns, M. Derrien and G. Leger in Hydrocarbon Processing, 1985 (3), pp. 51–59, teach the use of bimetallic catalysts, in particular ones comprising the metals of group VIII (current IUPAC nomenclature: groups 8, 9 and 10), especially palladium, and metals of group IB (current IUPAC nomenclature: group 11) of the Periodic Table of the Elements. EP-A 564 328 and EP-A 564 329 teach the use of catalysts comprising metals of group VIII, especially palladium, and metals of group IIIA (current IUPAC nomenclature: group 3), especially indium or gallium. EP-A 89 252 discloses a process for producing a palladium- and gold-containing supported catalyst and its use. DE-A 21 56 544 teaches a catalyst comprising palladium and zinc on a silica support. EP-A 722 776 discloses a catalyst which is particularly resistant to sulfur impurities and comprises palladium, at least one alkali metal fluoride and optionally silver on an inorganic support such as $TiO_2$, $ZrO_2$ or preferably $Al_2O_3$. EP-A 738 540 teaches a catalyst comprising palladium, silver, alkali metal and fluoride on an aluminum oxide support, with the ratio of fluoride to alkali metal being from 1.3:1 to 4:1.

It is also possible to influence the properties of the catalyst used not only by process engineering measures or the use of certain additives, but also by the type of support and the way in which the active composition is distributed on the internal and external surface area of the support.

Thus, DE-A 20 59 978 teaches palladium catalysts on an alumina (aluminum oxide) support. The support has a BET surface area of about 120 $m^2/g$ and, before deposition of the palladium, is first subjected to a treatment with steam at 110–300° C. and is subsequently calcined at 500–1200° C.

DE-A 31 19 850 discloses the use of a catalyst comprising palladium and silver on an $SiO_2$ support having a BET surface area in the range from 10 to 200 $m^2/g$ or on an $Al_2O_3$ support having a BET surface area of less than 100 $m^2/g$. The weight ratio of silver to palladium is generally in the range from 0.1 to 20 and, in specific embodiments, in the range from 0.7 to 3 or from 1 to 2.5. EP-A 780 155 and EP-A 686 615 disclose catalysts which comprise palladium and a metal of group IB of the Periodic Table of the Elements on an $Al_2O_3$ support, where at least 80% of the palladium and at least 80% of the metal of group IB are concentrated in the part of the catalyst particle which extends from the outside of the catalyst particle inward to a point whose distance from the center of the particle is 0.8 times the radius of the particle. Furthermore, in the case of the catalyst of EP-A 780 155, the metal of group IB and palladium are present in a weight ratio in the range from 0.4 to 3, and in the catalyst of EP-A 686 615 in a weight ratio in the range from 0.05 to 0.4. On the other hand, EP-A 64 301 teaches a palladium- and silver-containing catalyst in which only the palladium is concentrated in a layer near the surface and the silver is distributed uniformly over the catalyst volume and in which the silver and palladium are present in a weight ratio of at least 2.

The demands made of catalysts and processes for the selective hydrogenation of undesired unsaturated compounds in hydrocarbon streams in which they are present in respect of reducing the residual content of undesired unsaturated compounds after the hydrogenation and increasing the selectivity are continually rising. Although the known processes and catalysts have very high performance, they are still unsatisfactory in view of the increasing demands.

SUMMARY OF THE INVENTION

It is an object of the present invention to find an improved catalyst and an improved process for the selective hydrogenation of unsaturated compounds in hydrocarbon streams in which they are present and, in particular, for the selective hydrogenation of alkynes and/or alkadienes in C2 or C3 hydrocarbon streams.

We have found that this object is achieved by a catalyst comprising at least one metal of the 10th group of the Periodic Table of the Elements and at least one metal of the 11th group of the Periodic Table of the Elements on an aluminum oxide support, wherein the metal or metals of the 10th group is or are essentially concentrated in an outer layer close to the surface of the catalyst particle, the metal or metals of the 11th group is or are distributed essentially uniformly over the volume of the catalyst particle and the weight ratio of the metal or metals of the 11th group to the metal or metals of the 10th group is not more than 1.95.

Furthermore, we have found a process for producing this catalyst and a process for the selective hydrogenation of unsaturated compounds in hydrocarbon streams using the catalyst of the present invention.

DETAILED DESCRIPTION OF THE INVENTION

The catalyst of the present invention has excellent properties, in particular, in the selective hydrogenation of alkynes and alkadienes to form alkenes, especially a high selectivity when carrying out the process either in the mixed liquid and gas phase or in the pure gas phase. When the catalyst of the present invention is used, the undesirable overhydrogenation to form the saturated hydrocarbons such as ethane or propane can be reduced. In addition, the catalyst is comparatively active and can be operated over comparatively long periods of time. The catalyst of the present invention displays these advantageous properties even without further process engineering measures, for example without addition of carbon monoxide or alcohols, ethers or nitrogen-containing compounds. The catalyst of the present invention is particularly suitable for use as catalyst in the selective hydrogenation of acetylene in C2 streams to form ethylene or as catalyst in the selective hydrogenation of propyne and propadiene in C3 streams to form propylene.

The support used in the catalyst of the present invention comprises essentially aluminum oxide which, apart from unavoidable impurities, can further comprise some other additives. For example, other inorganic oxides such as oxides of metals of the 2nd, 3rd, 4th, 13th and 14th group of the Periodic Table of the Elements may be present, in particular silicon dioxide, titanium dioxide, zirconium dioxide, zinc oxide, magnesium oxide and calcium oxide. In general, such oxides other than aluminum oxide are present in amounts of less than 50% by weight, for example less than 30% by weight and preferably less than 10% by weight. Particularly preferably, the support consists of only aluminum oxide and unavoidable impurities. As aluminum oxide, use is made of the known aluminum oxide phases or the known partially hydrated aluminum oxide phases, for example $\alpha$-, $\beta$-, $\gamma$-, $\delta$-, $\theta$- or $\chi$-aluminum oxide, boehmite, pseudoboehmite or a mixture thereof.

BET surface area, pore volume and pore radius distribution (the proportion of pore volume as a function of pore diameter) of the support used for the catalyst of the present invention are optimized for the particular application in a manner known to those skilled in the art. The BET surface area of the support is generally from 2 to 200 $m^2/g$. It is for example at least 3 $m^2/g$ and preferably at least 4 $m^2/g$, and also, for example, at most 100 $m^2/g$, preferably at most 70 $m^2/g$ and particularly preferably at most 10 $m^2/g$. The total pore volume of the support is usually at least 0.1 ml/g, preferably at least 0.2 ml/g and particularly preferably at least 0.25 ml/g, and also at most 1.0 ml/g, preferably at most 0.5 ml/g and particularly preferably at most 0.4 ml/g. In general, at most 10% by volume, preferably at most 8% by volume, of the total pore volume is present in the form of pores having a mean diameter of at most 60 nanometers. Furthermore, the mean pore diameter is usually at least 50 nanometers, preferably at least 70 nanometers and at most 150 nanometers, preferably at most 130 nanometers.

The catalyst support is produced in a manner known to those skilled in the art; suitable supports are also commercially available. To produce the support, it is usual to mold a suitable aluminum-containing raw material, if desired after peptization using a peptizing agent such as water, dilute acid or dilute base, and then to dry and calcine the shaped bodies. Surface area and pore structure of the support are, as is known, determined essentially by the drying and calcination conditions together with the type of raw material used and any additions of materials which burn out, e.g. polymers, fibrous materials, natural materials which burn out such as ground nut shells or other customary additives. The shape of the support bodies is not important and it is possible to use all known shapes such as extrudates, rings, cylinders, hollow cylinders, shaped bodies having a star-like cross section, wagon wheels or spheres.

The catalyst comprises at least one metal of the 10th group of the Periodic Table of the Elements and at least one metal of the 11th group of the Periodic Table of the Elements. It can also further comprise additional additives and/or promoters.

The numbering of the groups of the Periodic Table of the Elements is based on the current numbering recommended by the International Union for Pure and Applied Chemistry (IUPAC). The 10th group consists of the elements nickel, palladium and platinum and the 11th group consists of the elements copper, silver and gold. As metal of the 10th group, the catalyst comprises nickel, palladium and/or platinum, for example palladium, preferably as sole metal of this group, and as metal of the 11th group comprises copper, silver and/or gold, for example silver, preferably as sole metal of this group. The catalyst preferably comprises palladium and silver and the active composition of the catalyst particularly preferably consists of palladium and silver.

The metals can be present in pure metallic form, or else in the form of compounds, for example in the form of metal oxides. Under the operating conditions of a hydrogenation process, they are generally present in the form of metals. The conversion of any oxides into metals can be carried out in a known manner prior to using the catalyst in a hydrogenation process by prereduction and, if necessary for manipulations involving the prereduced catalyst, subsequent surface passivation.

The metal or metals of the 10th group is or are essentially concentrated in an outer layer close to the surface of the support. In general, more than 80% by weight, preferably more than 90% by weight and particularly preferably more than 95% by weight, of the metal or metals is present in a layer which has a thickness of not more than 0.6 millimeters and is bounded by the geometric surface of the catalyst particle. This layer is preferably not thicker than 0.45 millimeters and particularly preferably not thicker than 0.3 millimeters.

The metal or metals of the 11th group is or are distributed essentially uniformly over the volume of the catalyst particle. Preferably, the content of metal or metals of the 11th group in the catalyst in each individual, representative volume element of a catalyst particle is always higher than 0.3 times and lower than two times, particularly preferably higher than 0.6 times and lower than 1.4 times, the integrated content of metal or metals of the 11th group in the catalyst. Here, the term "representative volume element" refers to a volume element which is smaller than the total catalyst particle but still has the macroscopic properties of the total particle, in particular the same specific pore volume, the same pore radius distribution and the same specific surface area.

The weight ratio of metal or metals of the 11th group to metal or metals of the 10th group is at most 1.95, for example at most 1.9, preferably at most 1.85 and particularly preferably at most 1.8. In addition, it is advantageously at least 0.45. It is, for example, at least 0.5, preferably at least 0.8 and particularly preferably at least 1.6.

The content of metal or metals of the 10th group of the Periodic Table of the Elements in the catalyst is generally at least 0.005% by weight, based on its total mass, preferably at least 0.01% by weight and particularly preferably at least 0.02% by weight. In general, this content is at most 1% by weight, preferably at most 0.5% by weight and particularly preferably at most 0.1% by weight. Although lower or higher contents are possible, they are normally economically unsatisfactory because their activity is too low or the raw material costs are too high.

For example, the catalyst of the present invention may contain 0.025 or 0.03% by weight of palladium.

The content of metal or metals of the 11th group of the Periodic Table of the Elements in the catalyst is determined automatically by the content of metal or metals of the 10th group and the weight ratio to the metal or metals of the 10th group to be set. Therefore, the catalyst preferably contains not more than 3.9% by weight, based on its total mass, of metal or metals of the 11th group, and advantageously at least 0.00225% by weight.

The catalyst can, if necessary or desired, further comprise other elements than the metals of the 10th and 11th groups of the Periodic Table of the Elements in its active composition. In particular, it may comprise customary promoters. Frequently used promoters are, for example, the alkali metals and alkaline earth metals, e.g. lithium, sodium, potassium, rubidium, cesium, magnesium, calcium, strontium and/or barium, and the elements of the 3rd group, e.g. gallium and/or indium, or other promoters such as zinc or fluoride. Type and amount of such promoters need to be optimized in a customary manner for the individual case; in general, the amounts of such promoters added are in the range from a few ppm by weight to a few thousand ppm by weight.

The metals and, if desired, promoters to be deposited on the support can be applied to the support by any known method which leads to uniform distribution of the metal or metals of the 11th group over the volume of the catalyst while at the same time leading to concentration of the metal or metals of the 10th group in an outer layer close to the surface of the catalyst particle. However, the preferred method is impregnation with a solution of the substances to be deposited and/or compounds which are converted into the substances to be deposited over the course of the further catalyst production. Impregnation processes for the deposition of active components, additives and/or dopants on a support, even nonuniformly distributed over the volume of the catalyst particle, are known to those skilled in the art. The individual substances to be deposited can be deposited individually and/or in partial amounts in a plurality of process steps or together and completely in one process step. Preference is given to joint deposition in one impregnation step. After the impregnation or after the individual impregnation steps, the impregnated support is dried and is converted into the ready-to-use catalyst by calcination and, if desired, other known after-treatment methods (for example activation and subsequent surface passivation).

The uniform distribution of the metal or metals of the 11th group over the volume of the catalyst particle with simultaneous concentration of the metal or metals of the 10th group in an outer layer close to the surface of the catalyst particle requires adherence to certain parameters during impregnation and the subsequent drying and, if applicable, calcination. Important parameters which have different influences on the uniform distribution or concentration of various metals are known to be, for example, the pH of the impregnation solution and the drying temperature.

In general, the support is impregnated with a solution of salts of the components to be deposited, and the volume of the solution is such that the solution is absorbed virtually completely by the pore volume of the support (incipient wetness method) but does not fully exhaust the absorption capability of the support for the impregnation solution. The impregnation solution can thus be used in an amount of less than 100%, for example not more than 95% by volume, not more than 90% by volume or not more than 85% by volume, of the liquid volume which can be absorbed by the support to be impregnated. The concentration of the salts in the solution is calculated such that, after impregnation and conversion of the impregnated support into the finished catalyst, the components to be deposited are present in the desired concentration in the catalyst. The salts are selected so that they leave no troublesome residues during production of the catalyst or its later use. Use is usually made of nitrates or ammonium salts.

The catalyst of the present invention is preferably produced by a process comprising a single-step impregnation of the support by the incipient wetness method with a nitric acid solution of the nitrates of the metals to be deposited. The concentration of the nitric acid used is at least high enough to give a clear solution. In general, the pH of the solution is not more than 5 and preferably not more than 2.

After the impregnation, the impregnated support is dried, generally at a temperature above 50° C. and below 120° C. The drying temperature is preferably above 60° C. and particularly preferably above 70° C., and preferably below 110° C. and particularly preferably below 100° C. It is, for example, 80° C. or thereabout. Drying is continued until water present in the impregnated support has been essentially completely removed, which is generally the case after a few hours. Usual drying times are in the range from one to 30 hours and depend on the drying temperature employed: a higher temperature shortens the drying time. Drying can also be further accelerated by using reduced pressure.

The dried catalyst is in principle ready to use: the deposited metal compounds can be reduced to the metals directly in the hydrogenation reactor by treatment with hydrogen or a hydrogen-containing gas. However, the catalyst is preferably calcined after drying. This calcination serves essentially to convert the salts applied into the components to be deposited or precursors of such components. In the case of impregnation with metal nitrates, the nitrates are essentially decomposed during the calcination to form metals and/or metal oxides which remain in the catalyst and nitrogen-containing gases which are given off. The metal compounds still present on the catalyst after calcination are subsequently reduced to the metals either during or before use of the catalyst in the hydrogenation reactor, automatically in the case of the hydrogenation or in a known manner beforehand.

The calcination temperature is generally at least 200° C. and at most 650° C. It is preferably at least 300° C. and particularly preferably at least 380° C. and preferably at most 550° C. and particularly preferably at most 520° C. The calcination time is in general at least 0.5 hours and at most 20 hours. The calcination is preferably carried out for at most 10 hours and particularly preferably at most 5 hours. The calcination is carried out in a customary furnace, for example in a rotary tube furnace, in a tunnel kiln or in a muffle furnace. The calcination can follow drying directly without intermediate cooling of the impregnated and dried support.

After the calcination, the catalyst is ready to use. If necessary or desired, it is activated by prereduction and, if desired, passivated again on its surface in a known manner before being used for the selective hydrogenation.

The selective hydrogenation process of the present invention involves the use of the catalyst of the present invention. The hydrogenation process of the present invention using the catalyst of the present invention is generally carried out in the same way as the known, heterogeneously catalyzed hydrogenation processes which serve for the same purpose. It can be carried out as a heterogeneously catalyzed gas-phase process in which both the hydrocarbon stream and the hydrogen for hydrogenation are present in the gas phase, or as a heterogeneously catalyzed gas/liquid-phase process in which the hydrocarbon stream is at least partly present as a liquid phase and the hydrogen is present in the gas phase and/or in dissolved form in the liquid phase. The parameters to be set, e.g. throughput of hydrocarbon stream, expressed as space velocity with the unit $[m^3/m^3*h]$, based on the catalyst volume, temperature and pressure, are selected in a manner analogous to that for the known processes.

The amount of hydrogen used, based on the amount of hydrocarbon stream fed to the reaction, depends on the amount and type of undesired unsaturated compounds present in the hydrocarbon stream. In general, the hydrogen is added in an amount ranging from 0.8 to 5 times the stoichiometrically required amount for complete reaction of hydrogen on passage through the reactor, preferably in the range from 0.95 to 2 times this amount. The hydrogenation of triple bonds normally proceeds faster than that of conjugated double bonds and the latter in turn react faster than unconjugated double bonds. This allows the process to be controlled by means of the amount of hydrogen added. The hydrogen may contain inerts, for example noble gases such as helium, neon or argon, other inert gases such as nitrogen, carbon dioxide and/or lower alkanes such as methane, ethane, propane and/or butane. Such inert gases in the hydrogen are preferably present in a concentration of less than 30% by volume. The hydrogen is preferably free of carbon monoxide.

The process can be carried out in one reactor or in a plurality of reactors connected in parallel or in series, in each case in a single pass or with recirculation. When the process is carried out in the gas/liquid phase, the hydrocarbon stream after passage through a reactor is usually freed of gases in a separator and part of the liquid obtained is recirculated to the reactor. The ratio of recirculated hydrocarbon stream to that fed into the reactor for the first time, known as the recycled ratio, is set such that the desired conversion is achieved under the other reaction conditions such as pressure, temperature, throughput and amount of hydrogen.

Applications of the process of the present invention are, in particular, the hydrogenation of alkynes and/or alkadienes to give alkenes, especially the selective hydrogenation of acetylene in C2 streams to give ethylene with minimal formation of ethane and the selective hydrogenation of propyne and/or propadiene in C3 streams to give propylene with minimal formation of propane.

The selective hydrogenation of acetylene in C2 streams to form ethylene is usually carried out as a gas-phase process at a space velocity of the gaseous C2 stream of from 500 $m^3/m^3*h$ to 10,000 $m^3/m^3*h$, based on the catalyst volume, at a temperature in the range from 0° C. to 250° C. and a pressure of from 0.01 bar to 50 bar, with at least one mol, preferably at least 1.2 mol, and at most 2 mol, preferably at most 1.8 mol, of hydrogen being added per mol of acetylene in the C2 stream.

The selective hydrogenation of propyne and/or propadiene in C3 streams to form propylene is usually carried out as a gas-phase process or as a gas/liquid-phase process at a space velocity of the liquid C3 stream of from 1 m³/m³*h to 50 m³/m³*h, based on the catalyst volume, at a temperature in the range from 0° C. to 180° C. and a pressure of from 0.01 bar to 50 bar, with from one to two mol of hydrogen being added per mol of propyne and propadiene in the C3 stream.

EXAMPLES

Example 1

Production of Catalyst 1

In a mixer, boehmite (Versal® 250, obtained from Euro Support, Amsterdam) was moistened with water, intensively milled in a pan mill until the mass was readily moldable and subsequently extruded to produce 3 mm extrudates. The extrudates were then dried for 2 hours at 120° C. and calcined for 2 hours at 1100° C. The extrudates (BET surface area: 100 m²/g) were then impregnated with an aqueous nitric acid solution (pH: 1.9) of silver nitrate and palladium nitrate at room temperature. The amount of impregnation solution was 90% by volume of the maximum amount which could be absorbed by the support used and the concentrations of the metal nitrates in the impregnation solution were set such that the catalyst finally contained 0.025% by weight of metallic palladium and 0.045% by weight of metallic silver. The weight ratio of silver to palladium was thus 1.8. The catalyst was dried at 80° C. and subsequently calcined at 400° C. Scanning electron microscopy (SEM) and EPMA (electron probe microanalysis) carried out on samples of the finished catalyst showed that silver was essentially distributed uniformly and palladium was concentrated in an outer layer close to the surface.

The catalyst produced in this way was designated as Catalyst 1.

Example 2

Production of Comparative Catalyst C1

Example 1 was repeated, but the concentrations of the metal nitrates in the impregnation solution were set such that a metal content in the finished catalyst of 0.03% by weight of palladium and 0.2% by weight of silver resulted. The weight ratio of silver to palladium was thus 6.7. Scanning electron microscopy (SEM) and EPMA (electron probe microanalysis) carried out on samples of the finished catalyst showed that silver was essentially uniformly distributed and palladium was concentrated in an outer layer close to the surface.

The catalyst produced in this way was designated as Comparative Catalyst C1.

Example 3

Production of Catalyst 2

In a mixer, two aluminum oxide powders having BET surface areas of 217 and 251 m²/g, tapped densities of 803 and 1018 g/l and losses on ignition of 3.7 and 25.1% by weight, respectively, were dry-mixed in a weight ratio of 3:2, moistened with dilute nitric acid and milled in a pan mill to give a readily moldable mass. This was extruded to form extrudates which were dried at 120° C. and calcined at 1150° C.

The extrudates (BET surface area: 6 m²/g) were then impregnated with an aqueous nitric acid solution (pH: 1.9) of silver nitrate and palladium nitrate at room temperature. The amount of impregnation solution was 90% by volume of the maximum amount which could be absorbed by the support used and the concentrations of the metal nitrates in the impregnation solution were set such that the final catalyst contained 0.025% by weight of metallic palladium and 0.045% by weight of metallic silver. The weight ratio of silver to palladium was thus 1.8. The catalyst was dried at 80° C. and subsequently calcined at 400° C. Scanning electron microscopy (SEM) and EPMA (electron probe microanalysis) carried out on samples of the finished catalyst showed that silver was essentially uniformly distributed and palladium was concentrated in an outer layer near the surface.

The catalyst produced in this way was designated as Catalyst 2.

Example 4

Production of Catalyst 3

Example 3 was repeated, but the concentrations of the metal nitrates in the impregnation solution were set such that a metal content in the finished catalyst of 0.03% by weight of palladium and 0.045% by weight of silver resulted. The weight ratio of silver to palladium was thus 1.5. Scanning electron microscopy (SEM) and EPMA (electron probe microanalysis) carried out on samples of the finished catalyst showed that silver was essentially uniformly distributed and palladium was concentrated in an outer layer near the surface.

The catalyst produced in this way was designated as Catalyst 3.

Example 5

Production of Comparative Catalyst C2

Example 3 was repeated, but the concentrations of the metal nitrates in the impregnation solution were set such that a metal content in the finished catalyst of 0.05% by weight of palladium and 0.025% by weight of silver resulted. The weight ratio of silver to palladium was thus 2.0. Scanning electron microscopy (SEM) and EPMA (electron probe microanalysis) carried out on samples of the finished catalyst showed that silver was essentially uniformly distributed and palladium was concentrated in an outer layer near the surface.

The catalyst produced in this way was designated as Comparative Catalyst C2.

Example 6

Hydrogenation Experiments

The performance of the Catalysts 1, 2, 3 and the Comparative Catalysts C1 and C2 in the hydrogenation of acetylene in an ethylene stream was tested in a laboratory plant using a fixed-bed reactor at atmospheric pressure. For this purpose, a model gas mixture of 99% by volume of ethylene and 1% by volume of acetylene was hydrogenated over 66 ml of the catalyst to be tested. Hydrogen was added to this gas mixture upstream of the reactor so that the gas stream fed to the reactor had a molar ratio of hydrogen to acetylene of 1.8. The temperature T of the reactor was set such that an acetylene conversion of 90 mol % was achieved. The analyses were carried out by means of a gas chromatograph. The throughput through the reactor which was set in each case, expressed as gas hourly space velocity (GHSV) of the total gas stream fed to the reactor, based on the volume of catalyst used, and the temperature set and the achieved selectivities S of the hydrogenation of acetylene to ethylene are shown in the table below.

| Cat. | BET surface area [m$^2$/g] | Weight ratio of Ag/Pd | GHSV [1/h] | T [° C.] | S [% by wt.] |
|---|---|---|---|---|---|
| 1 | 100 | 1.8 | 5400 | 85 | 33 |
| C1 | 100 | 6.7 | 5400 | 107 | 40 |
| 2 | 6 | 1.8 | 3000 | 63 | 35 |
| 3 | 6 | 1.5 | 3000 | 65 | 21 |
| C2 | 6 | 2.0 | 3000 | 65 | 15 |

Comparison of Catalyst 1 with Comparative Catalyst C1 shows that although an increase in the weight ratio of silver to palladium can lead to an increase in selectivity, the catalyst at the same time suffers a drastic decrease in activity which is extremely disadvantageous and uneconomical from an industrial point of view. Comparison of the Catalysts 2 and 3 with the Comparative Catalyst C2 shows that satisfactory selectivities combined with industrially advantageous and economically satisfactory activities can be achieved using the catalyst of the present invention.

We claim:

1. A catalyst comprising at least one metal of the 10th group of the Periodic Table of the Elements and at least one metal of the 11th group of the Periodic Table of the Elements on an aluminum oxide support, wherein the metal or metals of the 10th group is or are essentially concentrated in an outer layer close to the surface of the catalyst particle, the metal or metals of the 11th group is or are distributed essentially uniformly over the volume of the catalyst particle and the weight ratio of the metal or metals of the 11th group to the metal or metals of the 10th group is not more than 1.95.

2. A catalyst as claimed in claim 1 in which the metal or metals of the 10th group is or are present in an amount of at least 0.005% by weight and at most 2% by weight, based on the total weight of the catalyst.

3. A catalyst as claimed in claim 1 comprising palladium as metal of the 10th group.

4. A catalyst as claimed in claim 1 comprising silver as metal of the 11th group.

5. A catalyst as claimed in claim 1 comprising palladium as metal of the 10th group and silver as metal of the 11th group.

6. A process for producing a catalyst as described in claim 1 by impregnation of an aluminum oxide support with an aqueous nitric acid solution of salts of metals of groups 10 and 11, drying at a temperature in the range from 60° C. to 110° C. and calcination at a temperature in the range from 350° C. to 550° C.

* * * * *